United States Patent
Karimi et al.

(10) Patent No.: US 6,850,587 B1
(45) Date of Patent: Feb. 1, 2005

(54) REPROJECTION-BASED THREE-DIMENSIONAL IMAGE RECONSTRUCTION

(75) Inventors: Seemeen S. Karimi, Brookline, MA (US); Carl R. Crawford, Brookline, MA (US)

(73) Assignee: Analogic Corporation, Peabody, MA (US)

(*) Notice: Subject to any disclaimer, the term of this patent is extended or adjusted under 35 U.S.C. 154(b) by 241 days.

(21) Appl. No.: 10/279,412

(22) Filed: Oct. 24, 2002

Related U.S. Application Data

(60) Provisional application No. 60/343,776, filed on Oct. 24, 2001.

(51) Int. Cl.[7] ............................................... A61B 6/03
(52) U.S. Cl. ............................. 378/15; 378/8; 378/901
(58) Field of Search .......................... 378/4, 8, 15, 901

(56) References Cited

U.S. PATENT DOCUMENTS

| | | | |
|---|---|---|---|
| 5,377,250 A | 12/1994 | Hu | 378/15 |
| 5,390,111 A * | 2/1995 | Tam | 378/16 |
| 5,802,134 A | 9/1998 | Larson et al. | 378/4 |
| 6,009,142 A | 12/1999 | Sauer et al. | 378/15 |
| 6,574,297 B2 * | 6/2003 | Tam | 378/15 |

OTHER PUBLICATIONS

Kudo H., et al., *Quasi–Exact Filtered Backprojection Algorithm for Long–Object Problem in Helical Cone–Beam Tomography*, IEEE TMI, vol., No. 9, Sep. 2000.

Feldkamp, L.A., et al., *Practical cone–beam algorithm*, Journal of the Optical Society of America A, vol. 1, Jun. 1984.

Schaller, S., et al, *Exact Radon Rebinning Algorithm for the Long Object Problem in Helical Cone–Beam CT*, IEE TMI, vol. 19, No. 5, May 2000.

Wang, B. et al, *Generalized Feldkamp Image Reconstruction from Equiangular Cone–Beam Projection Data*.

Kudo, H., et al., *Cone–Beam Filtered–Backprojection Algorithm For Truncated Helical Data*, Phys. Med. Biol. 43 (1998), pp 2885–2909.

Defrise, M., et al, *A Solution to the Long–Object Problem in Helical Cone–Beam Tomography*, Phys. Med. Biol. 45 (2000), pp 623–643.

* cited by examiner

*Primary Examiner*—David V Bruce
(74) *Attorney, Agent, or Firm*—McDermott Will & Emery LLP

(57) ABSTRACT

A method of reconstructing a three-dimensional image from a set of X-ray projections generated by a scanning system, where the image corresponds to a first volume segment that is a portion of a longer object, includes reconstructing a first estimate image of a second volume segment larger than the first volume segment. The second volume segment includes the first volume segment. The method also includes applying a weighting function to the first estimate image for masking the first volume segment, so as to produce a hypothetical object image. The method further includes re-projecting the hypothetical object image so as to produce a set of simulated hybrid projections corresponding to the first volume segment. The method also includes reconstructing the hybrid projections so as to produce a three-dimensional image corresponding to the first volume segment.

30 Claims, 5 Drawing Sheets

REPROJECTION-BASED THREE-DIMENSIONAL IMAGE RECONSTRUCTION

CROSS-REFERENCE TO RELATED APPLICATIONS

This application is related to the following U.S. application, of common assignee, from which priority is claimed, and the contents of which are incorporated herein in their entirety by reference:

"REPROJECTION-BASED THREE-DIMENSIONAL IMAGE RECONSTRUCTION," U.S. Provisional Patent Application Ser. No. 60/343,776 filed Oct. 24, 2001.

STATEMENT REGARDING FEDERALLY SPONSORED RESEARCH

Not Applicable

REFERENCE TO MICROFICHE APPENDIX

Not Applicable

BACKGROUND OF THE INVENTION

The present invention relates to three-dimensional reconstruction of an image from a set of cone beam X-ray projections, and more particularly, to systems for and methods of reconstructing a three-dimensional image corresponding to a volume segment that is part of a longer object.

Three-dimensional (3D) reconstruction algorithms are being developed for future scanners characterized by large cone angles. These algorithms can be clinically useful only if they can be used to reconstruct a volume within the patient (i.e., a region of interest—"ROI"), without having to scan the entire length of the patient. If the entire length of the patient is not scanned, then data truncation occurs in the axial direction of the scan. This data truncation gives rise to a difficulty in image reconstruction referred to herein as the "long object problem," illustrated in FIG. 1. It is important to observe that this truncation is axial, i.e., perpendicular to the plane of the X-ray fan beam, and not within the plane of the fan beam. Thus, all of the data necessary to reconstruct the image slices within the ROI are present, even when the scan is limited to a volume slightly greater than the ROI.

Prior art reconstruction algorithms exist to solve the long-object problem, but the mathematical expressions of these algorithms are complicated and therefore difficult to implement. Such reconstruction algorithms typically handle the truncation that occurs at the edges of the ROI by either (1) imposing special conditions to include or exclude certain data, or (2) including boundary terms that are difficult to evaluate. Computer implementations of the special conditions or the boundary terms also give rise to image artifacts, partially due to the data quantization that occurs as a result of sampling.

It is an object of the present invention to substantially overcome the above-identified disadvantages and drawbacks of the prior art.

SUMMARY OF THE INVENTION

An improved image reconstruction technique, referred to herein as Re-projection based Three-dimensional Image Reconstruction (also referred to as "RETIRE") is disclosed. RETIRE may be represented by substantially simpler mathematical expressions, relative to the prior art reconstruction algorithms discussed herein. In general, RETIRE includes four steps. First, RETIRE reconstructs an initial image of a volume larger than the ROI using an approximate reconstruction algorithm. Next, RETIRE synthetically re-projects the re-constructed image in conjunction with a weighting function that "masks" the ROI. RETIRE then combines the measured projections and the re-projections to produce a set of hybrid projections corresponding to the ROI. Finally, RETIRE then reconstructs the hybrid projections using an existing reconstruction algorithm for a short object. The set of hybrid projections corresponding to the short object (i.e. the ROI) appears to be a complete scan of an object, so the existing reconstruction algorithm does not encounter the truncation problems discussed herein. The short object problem is illustrated in FIG. 2.

In one aspect, the invention comprises a method of reconstructing a three-dimensional image from a set of X-ray projections generated by a scanning system. The image corresponds to a first volume segment that is a portion of a longer object. The method includes reconstructing, from the set of X-ray projections, a first estimate image of a second volume segment larger than the first volume segment. The second volume segment includes the first volume segment. The method also includes applying a weighting function to the first estimate image for masking the first volume segment, so as to produce a hypothetical object image. The method further includes re-projecting the hypothetical object image so as to produce a set of simulated projections. The method includes combining the original projections with the reprojections of the hypothetical object to produce hybrid projections of the first volume segment only. The method also includes reconstructing the hybrid projections so as to produce a three-dimensional image corresponding to the first volume segment.

Another embodiment further includes reconstructing a first estimate image of the second volume segment via an approximate reconstruction algorithm such as a Helical Feldkamp algorithm.

Another embodiment further includes reconstructing a first estimate image of the second volume segment via an approximate reconstruction algorithm such as a nutating slice reconstruction algorithm.

Another embodiment further includes reconstructing a first estimate image of a second volume segment larger than the first volume segment. The first volume segment is disposed in a middle portion of the second volume segment, such that a first region, ROI, includes an intersection of the first volume segment and the second volume segment. A second region, $\overline{\text{ROI}}$, includes portions of the second volume that do not intersect the first volume.

Another embodiment further includes extending and tapering the first volume into the second volume.

Another embodiment further includes extending the second region $\overline{\text{ROI}}$ to a predetermined distance from the first region ROI. The predetermined distance is chosen such that the hybrid projections are reduced to zero at the end of the second region $\overline{\text{ROI}}$.

Another embodiment further includes applying a set of binary coefficients to the first estimate image, so as to produce a hypothetical object image.

Another embodiment further includes applying binary coefficients substantially equal to zero to portions of the first estimate image corresponding to the first volume segment, and applying binary coefficients substantially equal to one elsewhere.

Another embodiment further includes re-projecting the hypothetical object via a computer simulation using parameters corresponding to the geometry of the scanning system.

Another embodiment further includes simulating the scanning system so as to reproduce one or more relationships among the hypothetical object, a simulated X-ray source, and a simulated detector array. The one or more relationships derive from the scanning system.

Another embodiment further includes combining the original and simulated re-projections to produce hybrid projections. The simulated projections are preferably subtracted from the original projections. The projection data in the hybrid projections corresponding to the volume outside the second volume are masked to zero.

Another embodiment further includes reconstructing the hybrid projections by executing a Radon transform inversion.

Another embodiment further includes reconstructing the hybrid projections by executing a filtered back-projection algorithm.

In another aspect, the invention comprises a system for reconstructing a three-dimensional image from a set of X-ray projections generated by a scanning system. The image corresponds to a first volume segment that is a portion of a longer object. The system includes a first reconstruction processor for reconstructing, from the set of X-ray projections, a first estimate image of a second volume segment larger than the first volume segment, wherein the second volume segment includes the first volume segment. The system further includes a masking processor for applying a weighting function to the first estimate image for masking the first volume segment, so as to produce a hypothetical object image. The system also includes a re-projection processor for re-projecting the hypothetical object image so as to produce a set of simulated hybrid projections corresponding to the first volume segment. The system also includes a combination processor to combine the original projections with the re-projections to produce hybrid projections. The system also includes a second reconstruction processor for reconstructing the hybrid projections so as to produce a three-dimensional image corresponding to the first volume segment.

In another embodiment, the first reconstruction processor reconstructs a first estimate image of the second volume segment via an approximate reconstruction algorithm such as a Helical Feldkamp algorithm.

In another embodiment, the first reconstruction processor reconstructs a first estimate image of the second volume segment via an approximate reconstruction algorithm such as a nutating slice reconstruction algorithm.

In another embodiment, the first reconstruction processor reconstructs a first estimate image of a second volume segment larger than the first volume segment. The first volume segment is disposed in a middle portion of the second volume segment, such that a first region ROI includes an intersection of the first volume segment and the second volume segment. A second region $\overline{ROI}$ includes portions of the second volume that do not intersect the first volume.

In another embodiment, the first volume extends and tapers into the second volume.

In another embodiment, the second region $\overline{ROI}$ extends from the first region ROI by a predetermined distance chosen such that the hybrid projections are reduced to zero at the end of the second region $\overline{ROI}$.

In another embodiment, the masking processor applies a set of binary coefficients to the first estimate image, so as to produce a hypothetical object image.

In another embodiment, the masking processor applies binary coefficients substantially equal to zero to portions of the first estimate image corresponding to the first volume segment, and applying binary coefficients substantially equal to one elsewhere.

In another embodiment, the re-projection processor re-projects the hypothetical object via a computer simulation using parameters corresponding to the geometry of the scanning system.

In another embodiment, the re-projection processor simulates the scanning system so as to reproduce one or more relationships among the hypothetical object, a simulated X-ray source, and a simulated detector array. The one or more relationships derive from the scanning system.

In another embodiment, the combination processor combines the original projections (i.e., those generated by the scanning system) and re-projections to produce hybrid projections of the ROI. The simulated projections are preferably subtracted from the original projections, although alternative embodiments may use other mathematical combinations. The projection data in the hybrid projections corresponding to the volume outside the second volume are masked to zero.

In another embodiment, the second reconstruction processor reconstructs the hybrid projections by executing a Radon transform inversion.

In another embodiment, the second reconstruction processor reconstructs the hybrid projections by executing a filtered back-projection algorithm.

In another embodiment, the second reconstruction processor is substantially more complex as compared to the first reconstruction processor and provides a substantially higher quality image as compared to an image generated by first reconstruction algorithm processor.

In another aspect, the invention comprises a system for reconstructing a three-dimensional image from a set of X-ray projections generated by a scanning system. The image corresponds to a first volume segment that is a portion of a longer object. The system includes means for reconstructing, from the set of X-ray projections, a first estimate image of a second volume segment larger than the first volume segment, wherein the second volume segment includes the first volume segment. The system further includes means for applying a weighting function to the first estimate image for masking the first volume segment, so as to produce a hypothetical object image. The system also includes means for re-projecting the hypothetical object image so as to produce a set of simulated hybrid projections corresponding to the first volume segment. The system further includes means for reconstructing the hybrid projections so as to produce a three-dimensional image corresponding to the first volume segment.

BRIEF DESCRIPTION OF DRAWINGS

The foregoing and other objects of this invention, the various features thereof, as well as the invention itself, may be more fully understood from the following description, when read together with the accompanying drawings in which.

DESCRIPTION OF THE PREFERRED EMBODIMENTS

Figure 1:
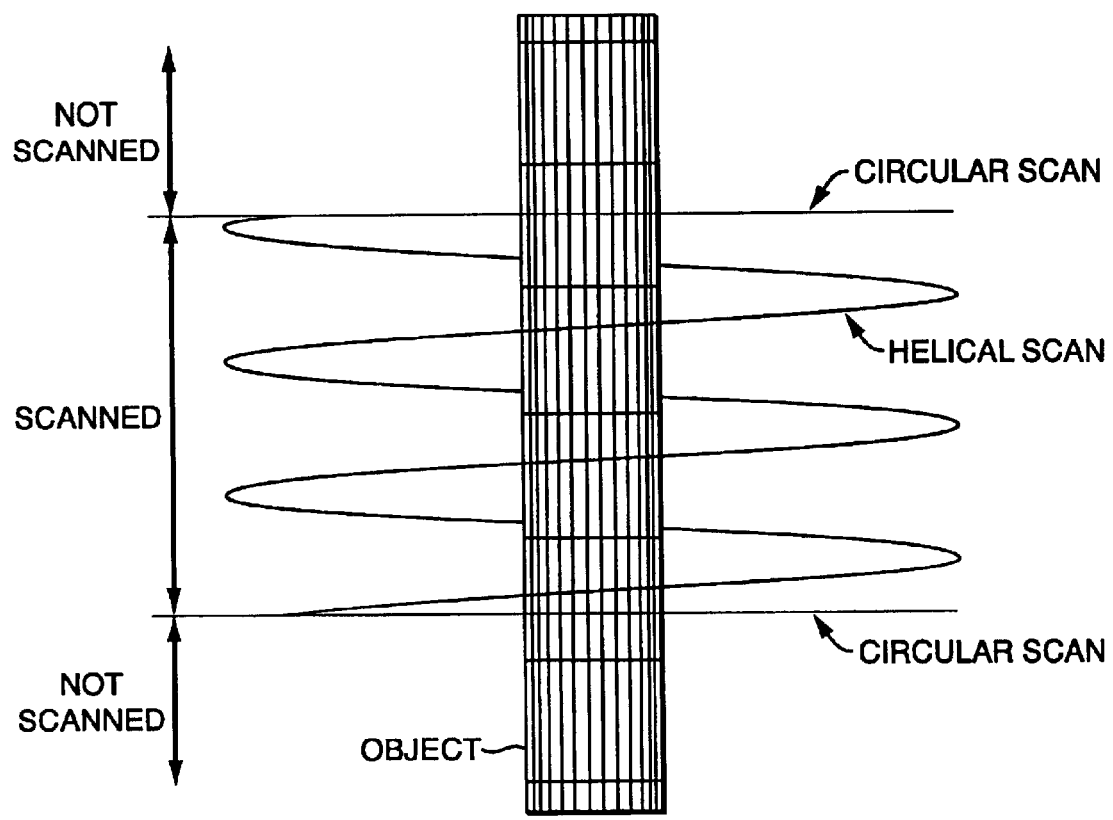
FIG. 1 shows a potential image reconstruction difficulty referred to herein as the long object problem.
Figure 2:
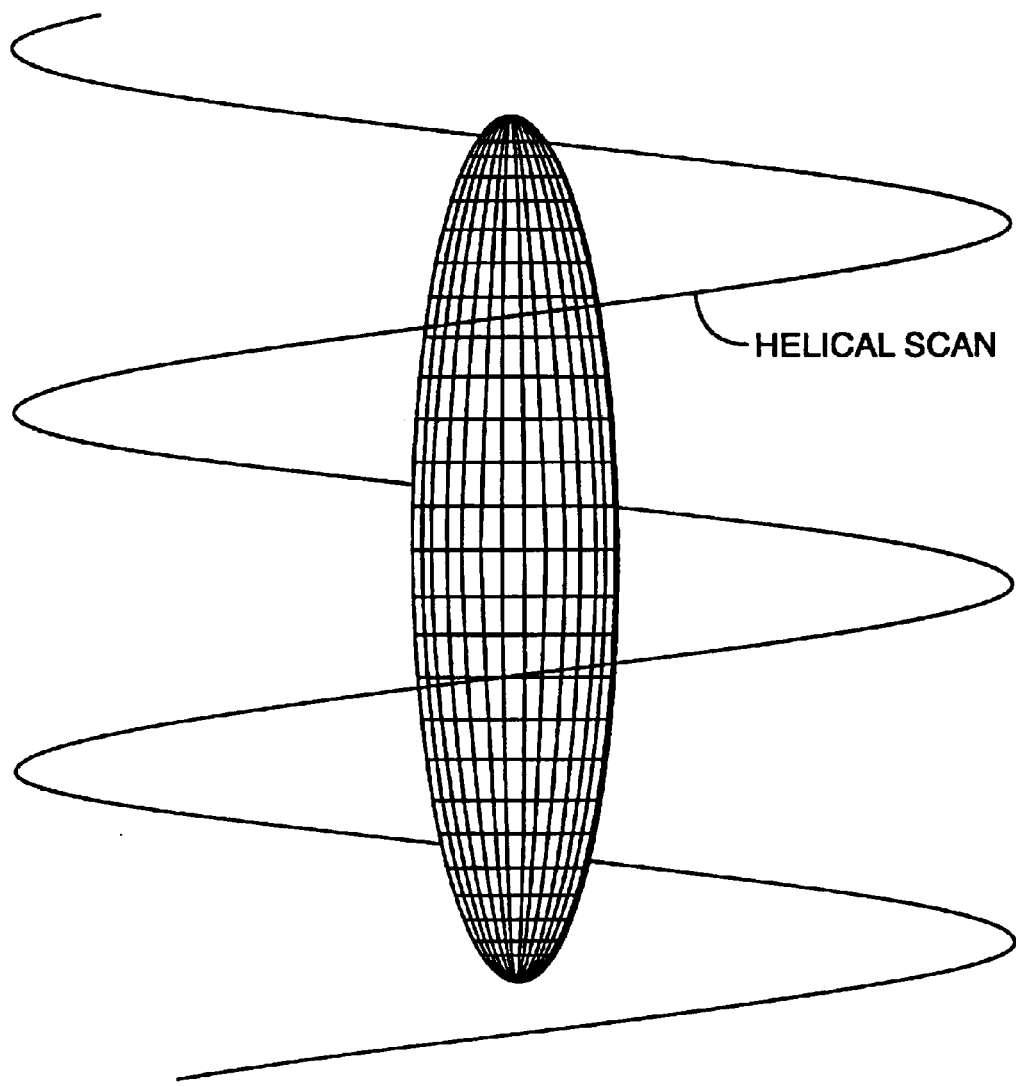
FIG. 2 illustrates the hypothetical short object problem described herein.
Figure 3:
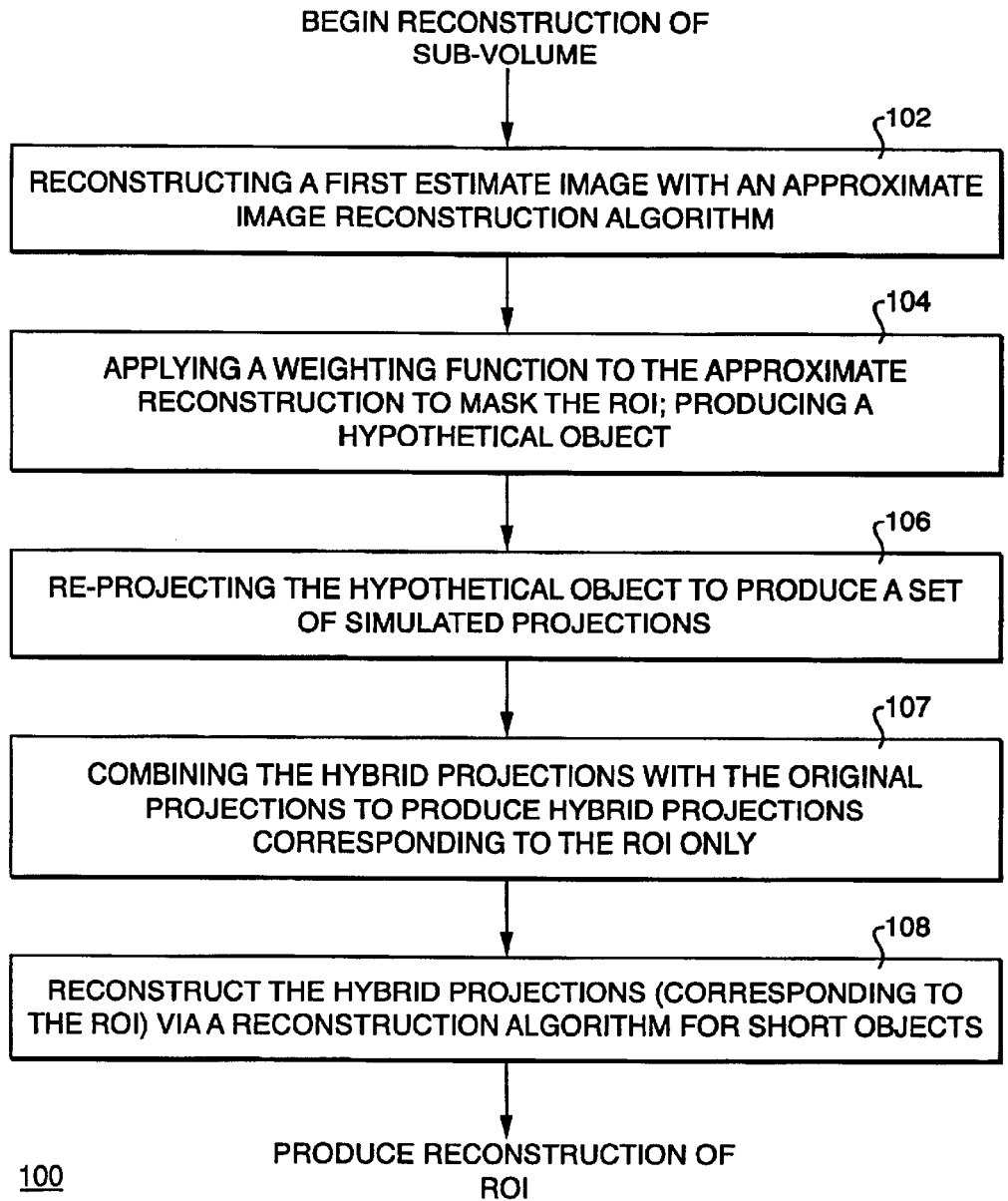
FIG. 3 shows a flow diagram of one preferred embodiment of an improved image reconstruction method according to the present invention.

FIG. 3 shows a flow diagram of one preferred embodiment of an improved image reconstruction method 100 according to the present invention. This method 100 takes advantage of the fact that reconstruction is a linear process, such that the image corresponding to the difference between two objects can be reconstructed from the difference between the projections of the two objects. For the purposes of this method 100, the entire long object (i.e., total volume that the CT system scans) is one of the two objects, and a synthesized hypothetical object is the other of the two objects. The hypothetical object is synthesized such that the difference between the two objects is a short object corresponding to the ROI. The difference between the projections of the long object and the hypothetical object results in the projections of the short object. The critical aspect of ROI is that it may be considered a short object that has been completely scanned, for the purposes of reconstruction. In other words, although the ROI (e.g., a specific region of the patient) is in actuality a sub-section of a long object (e.g., the patient), the ROI may be treated as a short object by virtue of how the projection data are generated. Since this ROI may be treated as a short object, a relatively simple reconstruction algorithm may be used to reconstruct the image from the associated projections, without incurring degradation at the boundaries.

Figures 4A, 4B:
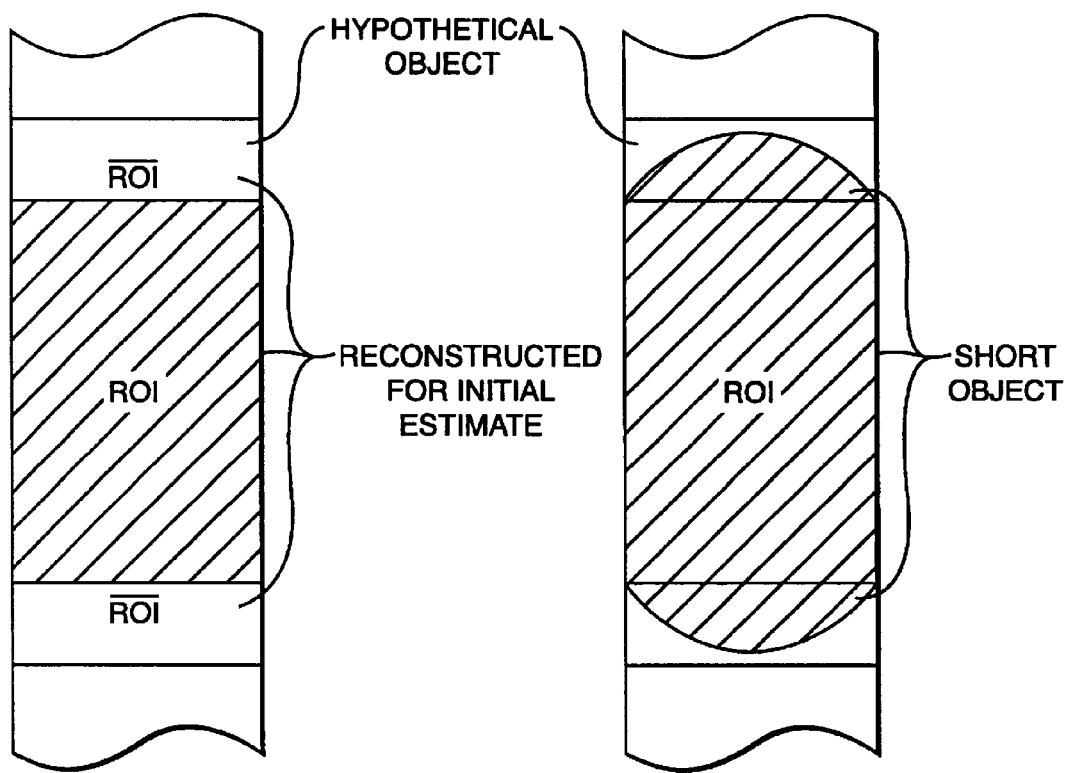
FIG. 4A shows the ROI and the volume outside the ROI, designated as $\overline{\text{ROI}}$, which must also be reconstructed to give the first estimate image.
FIG. 4B shows an extended and tapered short object from FIG. 4A.

The method of FIG. 3 comprises four steps. The first step 102 includes reconstructing a first estimate image with an approximate image reconstruction algorithm. In one embodiment, the algorithm used to generate an approximate reconstruction may include the Helical Feldkamp (see, for example, Wang, B., Liu, H., Wang, G., "Generalized Feldkamp Image Reconstruction from Equiangular Cone Beam Projection Data; Hu, H., "Reconstruction method for helical scanning computed tomography apparatus with multi-row detector array," U.S. Pat. No. 5,377,250, or Feldkamp, L., Davis, L., Kress, J., "Practical cone-beam algorithm," Journal of the Optical Society of America A, Vol. 1, p. 612, June 1984). In another embodiment, the reconstruction algorithm used to generate an approximate image may include a nutating slice reconstruction (NSR) algorithm (see, for example, Larson G., Ruth, C., and Crawford, C., "Nutating Slice CT Image Reconstruction Apparatus and Method," U.S. Pat. No. 5,802,134). This initial step includes reconstructing a volume that is greater than the ROI, as shown in FIGS. 4A and 4B. FIG. 4A shows the ROI and the volume outside the ROI, designated as $\overline{\text{ROI}}$, which must also be reconstructed to give the first estimate image.

The second step 104 of the method of FIG. 3 is applying a weighting function to the approximate reconstruction to "mask" the ROI. In one embodiment the weighing function includes a set of binary weighting coefficients. The weighting coefficients corresponding to the ROI are zero (or near zero), and the weighting coefficients corresponding to the volume outside of the ROI are at (or near) unity. This weighting thus blanks out the volume of the approximate reconstruction corresponding to the ROI, and leaves the other regions of the approximate reconstruction unaffected. The weighted reconstruction is the image of the hypothetical object, $\overline{\text{ROI}}$.

The third step 106 of the method of FIG. 3 is re-projecting the hypothetical object that results from the second step, using the same geometry as the original scanning system. Re-projection occurs via a computer simulation that mimics the actual scanning system. The simulation operates on the hypothetical object to produce a set of simulated projections (referred to herein as "re-projections"). The simulation relies on predetermined parameters that define relationships among the hypothetical object, the simulated X-ray source, and the simulated detector array. These relationships among the simulated components preferably match the relationships among the corresponding actual components in the scanning system. The fourth step 107 of the method of FIG. 3 is subtracting the resulting re-projections from the original projections acquired in the first step; the difference is referred to herein as the "hybrid projections." The hybrid projections are substantially equal to zero at the ends of the second volume. The projection values are forced to zero beyond the appearance of values approximately equal to zero after subtraction. Forcing hybrid projection data to zero ensures that in case the hybrid scan extends further than the point where the rays correspond to $\overline{\text{ROI}}$ alone, the hybrid projections will again assume the value of the original projections. After forcing these projections to zero, the hybrid projections correspond to the projections of the short object that is identical to the long object within the ROI, and zero outside of the ROI.

In the fifth step 108 of the method of FIG. 3, the hybrid projections are reconstructed using a reconstruction algorithm for short objects. There are several different types of such reconstruction algorithms known in the art. One example is a Radon transform inversion (see, for example, Schaller, S., Noo, F., Sauer, K., Tam, K., Lauritsch, G., and Flohr, T., "Exact Radon Rebinning Algorithm for the Long Object Problem in Helical Cone-Beam CT," IEEE TMI, Vol. 19, No. 5, May, 2000). Another example is a filtered back-projection algorithm (see, for example, Kudo, H., Noo, F., Defrise, M., "Cone beam filtered back-projection algorithm for truncated helical data," Phys. Med. Biol. 43, (1998) pp. 2885–2909, May 1998). Other reconstruction algorithms known in the art for reconstructing short objects may also be used.

Figure 5:
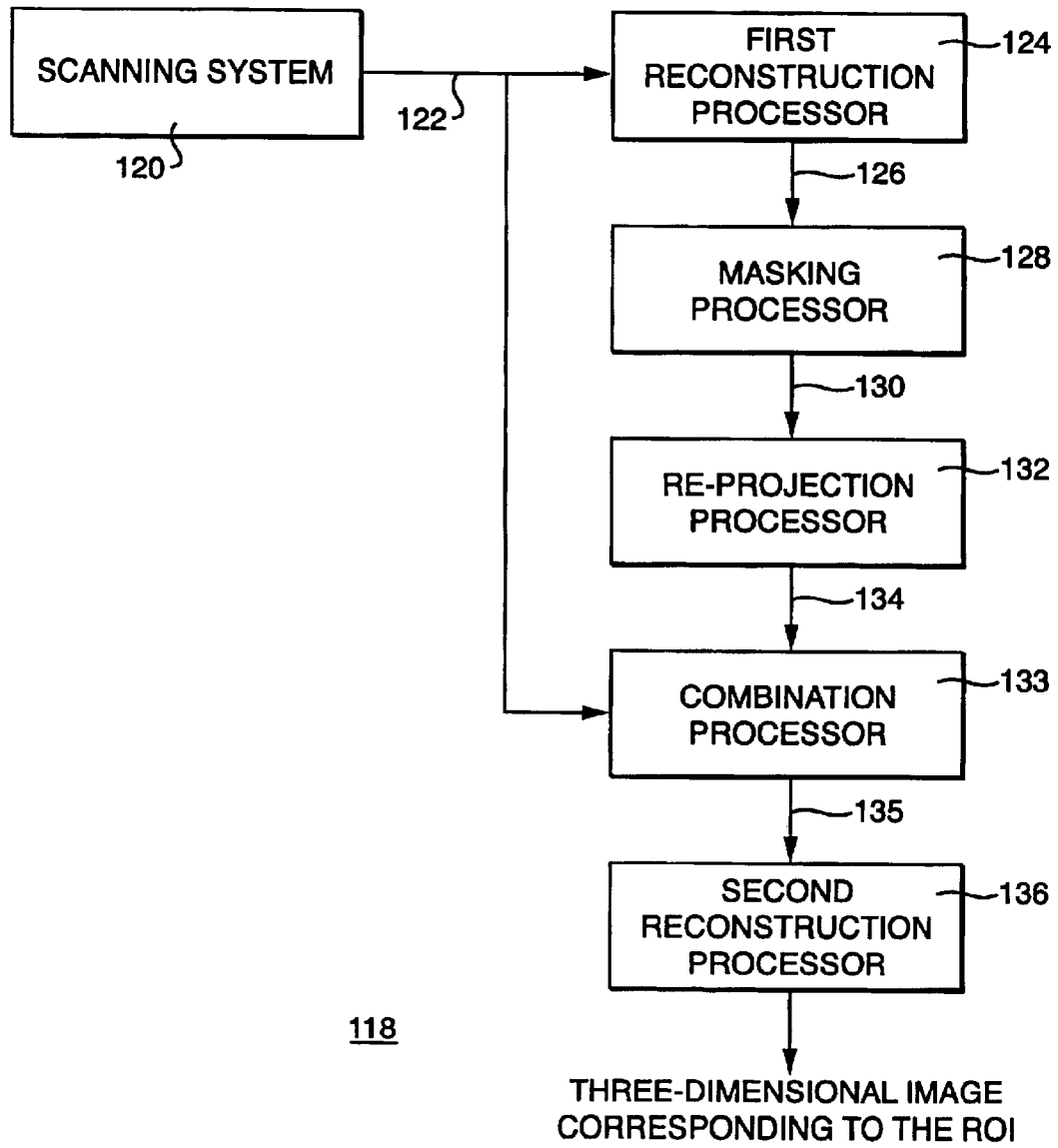
FIG. 5 shows a flow diagram of one preferred embodiment of an improved image reconstruction method according to the present invention.

FIG. 5 shows a block diagram view of one embodiment of a system 118 for reconstructing a three dimensional image from a set of X-ray projections according to the present invention. A scanning system 120 provides a set of X-ray projections 122 to a first reconstruction processor 124, which reconstructs a first estimate image 126 of a second volume segment that is larger than the ROI. The first reconstruction processor 124 passes the first estimate image 126 to a masking processor 128, which applies a weighting function to the first estimate image 126 to mask the ROI, so as to produce a hypothetical image 130. The masking processor 128 passes the hypothetical image 130 to the re-projection processor 132, which produces a set of simulated projections 134 by simulating the scanning system 120. The re-projection processor 132 passes the simulated projections to a combination processor 133, which combines the original projections 122 with the simulated projections 134 to produce a set of hybrid projections 135. The combination processor 133 passes the hybrid projections 135 to the second reconstruction processor 136, which reconstructs the hybrid projections 135 so as to produce a three-dimensional image corresponding to the ROI.

The hybrid projections from the third step of the method of FIG. 3 contain exactly the measured projection values in the cone beam projections of the ROI. In the projections of the volume $\overline{ROI}$ the hybrid projections contain the difference between the measured projections and re-projections of the weighted object.

For an exact reconstruction of the ROI, the method described in FIG. 3 assumes that the re-projections of the hypothetical object are exactly equal to the measured projections of the hypothetical object. Therefore, it assumes that the process of reconstruction and re-projection do not introduce their own transfer functions into the data. In reality, in the hybrid projections, the component due to the volume in the ROI will be identical to the measured projections, but the component due to the $\overline{ROI}$ will not be identical to the measured projections because of the finite transfer functions associated with reconstruction and re-projection. Therefore, the difference of the measured and re-projected data from $\overline{ROI}$ will leave a residual instead of zero. Due to the three dimensional nature of the re-projections, some of the hybrid projections will contain data from ROI and $\overline{ROI}$. Therefore the hybrid projections will contain three types of data, measured projections from the region ROI alone, projections of ROI and $\overline{ROI}$, and projections of $\overline{ROI}$ alone. The accuracy of the projections gets progressively worse as the contribution from the ROI decreases and the contribution from $\overline{ROI}$ increases.

The hybrid projections will be reconstructed to give the short object. It is desirable to (i) minimize the residuals, because residuals behave as data inconsistencies that will add artifacts to the image; and (ii) minimize the derivative of the Radon transform at the edges, because any filtering across sharp (i.e., abruptly changing) edges will add artifacts to the image. One way to achieve both goals simultaneously is to extend and taper the short object into the second volume, i.e. extend ROI into $\overline{ROI}$. FIG. 4B shows an extended and tapered short object. Now the hybrid projections will be more accurate because the measured projections contribute more than the synthetic projections. Also, the derivative of the Radon transform along any direction will be continuous.

In order to approximately reconstruct the initial estimate, consisting of ROI and $\overline{ROI}$, the source trajectory must extend beyond the limits in the axial direction. The extra distance depends on the approximate algorithm used, and the cone angle. We know that projections of a short object will be reduced to zero at the beginning and end of the scan. Therefore, the hybrid projections must be reduced to zero at the beginning and end of the scan. For this, the region $\overline{ROI}$ should be long enough that the hybrid projections reduce to zero.

The method disclosed herein and described in FIG. 3 has certain advantages and disadvantages over previously published algorithms for long object reconstruction. Its advantage is its simplicity. It has no complicated special conditions or boundary terms to implement. Secondly, it provides data that has smooth derivatives, and is less prone to sampling artifacts for that reason. The method, however, may be more time-consuming than long object reconstruction algorithms in the prior art, because it reconstructs images twice and uses re-projection as well. Even though each reconstruction step may be pipelined, the underlying algorithm is not pipelined, since by definition, all the data must be present before the second reconstruction step begins. Further, the method may produce artifacts due to residuals, even with the tapering in the $\overline{ROI}$ as described above.

The invention may be embodied in other specific forms without departing from the spirit or essential characteristics thereof. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. A method of reconstructing a three dimensional image from a set of X-ray projections generated by a scanning system, the image corresponding to a first volume segment that is a portion of a longer object, comprising:

reconstructing, from the set of X-ray projections, a first estimate image of a second volume segment larger than the first volume segment, wherein the second volume segment includes the first volume segment;

applying a weighting function to the first estimate image for masking the first volume segment, so as to produce a hypothetical object image;

re-projecting the hypothetical object image so as to produce a set of simulated projections;

combining the projections generated by the scanning system and simulated re-projections to give hybrid projections corresponding to the first volume segment only;

reconstructing the hybrid projections so as to produce a three dimensional image corresponding to the first volume segment.

2. A method according to claim 1, further including reconstructing a first estimate image of the second volume segment via an approximate reconstruction algorithm including a Helical Feldkamp algorithm.

3. A method according to claim 1, further including reconstructing a first estimate image of the second volume segment via an approximate reconstruction algorithm including a nutating slice reconstruction algorithm.

4. A method according to claim 1, further including reconstructing a first estimate image of a second volume segment larger than the first volume segment, wherein (i) the first volume segment is disposed in a middle portion of the second volume segment, such that a first region ROI includes an intersection of the first volume segment and the second volume segment, and a second region $\overline{ROI}$ includes portions of the second volume segment that do not intersect the first volume.

5. A method according to claim 4, further including extending and tapering the first volume into the second region $\overline{ROI}$.

6. A method according to claim 4, further including extending the second region $\overline{ROI}$ to a predetermined distance from the first region ROI, the predetermined distance chosen such that the hybrid projections are reduced to zero at the end of the second region $\overline{ROI}$.

7. A method according to claim 1, further including applying a set of binary coefficients to the first estimate image, so as to produce a hypothetical object image.

8. A method according to claim 7, further including applying binary coefficients substantially equal to zero to portions of the first estimate image corresponding to the first volume segment, and applying binary coefficients substantially equal to one elsewhere.

9. A method according to claim 1, further including re-projecting the hypothetical object via a computer simulation using parameters corresponding to the geometry of the scanning system.

10. A method according to claim 9, further including simulating the scanning system so as to reproduce one or more relationships among the hypothetical object, a simulated X-ray source, and a simulated detector array, wherein the one or more relationships derive from the scanning system.

11. A method according to claim 1, further including subtracting the simulated re-projections from the projections generated by the scanning system to produce hybrid projections and masking the hybrid projections beyond those projection values substantially equal to zero.

12. A method according to claim 1, further including reconstructing the hybrid projections by executing a Radon transform inversion.

13. A method according to claim 1, further including reconstructing the hybrid projections by executing a filtered back-projection algorithm.

14. A system for reconstructing a three dimensional image from a set of X-ray projections generated by a scanning system, the image corresponding to a first volume segment that is a portion of a longer object, comprising:
 a first reconstruction processor for reconstructing, from the set of X-ray projections, a first estimate image of a second volume segment larger than the first volume segment, wherein the second volume segment includes the first volume segment;
 a masking processor for applying a weighting function to the first estimate image for masking the first volume segment, so as to produce a hypothetical object image;
 a re-projection processor for re-projecting the hypothetical object image so as to produce a set of simulated projections;
 a combination processor for combining the projections generated by the scanning system and the simulated projections to produce a set of hybrid projections corresponding to the first volume segment;
 a second reconstruction processor for reconstructing the hybrid projections so as to produce a three dimensional image corresponding to the first volume segment.

15. A system according to claim 14, wherein the first reconstruction processor reconstructs a first estimate image of the second volume segment via an approximate reconstruction algorithm including a Helical Feldkamp algorithm.

16. A system according to claim 14, wherein the first reconstruction processor reconstructs a first estimate image of the second volume segment via an approximate reconstruction algorithm including a nutating slice reconstruction algorithm.

17. A system according to claim 14, wherein the first reconstruction processor reconstructs a first estimate image of a second volume segment larger than the first volume segment, and (i) the first volume segment is disposed in a middle portion of the second volume segment, such that a first region ROI includes an intersection of the first volume segment and the second volume segment, and a second region $\overline{ROI}$ includes portions of the second volume that do not intersect the first volume.

18. A system according to claim 17, wherein the first volume extends and tapers into the second region $\overline{ROI}$.

19. A system according to claim 17, wherein the second region $\overline{ROI}$ extends from the first region ROI by a predetermined distance chosen such that the hybrid projections are reduced to zero at the end of the second region $\overline{ROI}$.

20. A system according to claim 14, wherein the masking processor applies a set of binary coefficients to the first estimate image, so as to produce a hypothetical object image.

21. A system according to claim 20, wherein the masking processor applies binary coefficient s substantially equal to zero to portions of the first estimate image corresponding to the first volume segment, and applying binary coefficients substantially equal to one elsewhere.

22. A system according to claim 14, wherein the re-projection processor re-projects the hypothetical object via a computer simulation using parameters corresponding to the geometry of the scanning system.

23. A system according to claim 22, wherein the re-projection processor simulates the scanning system so as to reproduce one or more relationships among the hypothetical object, a simulated X-ray source, and a simulated detector array, where in the one or more relationships derive from the scanning system.

24. A system according to claim 14, wherein the combination processor subtracts the simulated projections from the original projections generated by the scanning system to produce hybrid projections, and masks the hybrid projections beyond those projection values substantially equal to zero.

25. A system according to claim 14, wherein the second reconstruction processor reconstructs the hybrid projections by executing a Radon transform inversion.

26. A system according to claim 14, wherein the second reconstruction processor reconstructs the hybrid projections by executing a filtered back-projection algorithm.

27. A system according to claim 14, wherein the second reconstruction processor is substantially more complex as compared to the first reconstruction processor and provides a substantially higher quality image as compared to an image generated by first reconstruction algorithm processor.

28. A system for reconstructing a three dimensional image from a set of X-ray projections generated by a scanning system, the image corresponding to a first volume segment that is a portion of a longer object, comprising:
 means for reconstructing, from the set of X-ray projections, a first estimate image of a second volume segment larger than the first volume segment, wherein the second volume segment includes the first volume segment;
 means for applying a weighting function to the first estimate image for masking the first volume segment, so as to produce a hypothetical object image;
 means for re-projecting the hypothetical object image so as to produce a set of simulated hybrid projections corresponding to the first volume segment;
 means for reconstructing the hybrid projections so as to produce a three dimensional image corresponding to the first volume segment.

29. A method of reconstructing a three dimensional image from a set of X-ray projections generated by a scanning system, the image corresponding to a first volume segment that is a portion of a longer object, comprising:
 reconstructing, via an approximate reconstruction algorithm including a Helical Feldkamp algorithm, a first estimate image of a second volume segment larger than the first volume segment, wherein the second volume segment includes the first volume segment, the second volume segment is larger than the first volume segment, and (i) the first volume segment is disposed in a middle portion of the second volume segment, such that a first region ROI includes an intersection of the first volume segment and the second volume segment, and a second region $\overline{ROI}$ include those portions of the second volume that do not intersect the first volume;

applying a weighting function to the first estimate image for masking the first volume segment, so as to produce a hypothetical object image, by applying binary coefficients substantially equal to zero to portions of the first estimate image corresponding to the first volume segment, and applying binary coefficients substantially equal to one elsewhere;

re-projecting the hypothetical object image, via a computer simulation using parameters corresponding to the geometry of the scanning system, so as to produce a set of simulated hybrid projections corresponding to the first volume segment;

reconstructing the hybrid projections by executing a Radon transform inversion or a filtered back-projection algorithm so as to produce a three dimensional image corresponding to the first volume segment.

30. A system for reconstructing a three dimensional image from a set of X-ray projections generated by a scanning system, the image corresponding to a first volume segment that is a portion of a longer object, comprising:

a first reconstruction processor for reconstructing, from the set of X-ray projections and via an approximate reconstruction algorithm including a Helical Feldkamp algorithm, a first estimate image of a second volume segment larger than the first volume segment, wherein the second volume segment includes the first volume segment, the second volume segment is larger than the first volume segment, and (i) the first volume segment is disposed in a middle portion of the second volume segment, such that a first region ROI includes an intersection of the first volume segment and the second volume segment, and a second region $\overline{ROI}$ include those portions of the second volume that do not intersect the first volume;

a masking processor for applying a weighting function to the first estimate image for masking the first volume segment, so as to produce a hypothetical object image, by applying binary coefficients substantially equal to zero to portions of the first estimate image corresponding to the first volume segment, and applying binary coefficients substantially equal to one elsewhere;

a re-projection processor for re-projecting the hypothetical object image, via a computer simulation using parameters corresponding to the geometry of the scanning system, so as to produce a set of simulated hybrid projections corresponding to the first volume segment;

a second reconstruction processor for reconstructing the hybrid projections by executing a Radon transform inversion or a filtered back-projection algorithm so as to produce a three dimensional image corresponding to the first volume segment.

* * * * *